(12) United States Patent
Wullenweber

(10) Patent No.: US 9,788,802 B2
(45) Date of Patent: Oct. 17, 2017

(54) METHOD FOR ASCERTAINING AN ABSOLUTE SCAN REGION ON A PATIENT

(71) Applicant: Siemens Aktiengesellschaft, Munich (DE)

(72) Inventor: Michael Wullenweber, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 68 days.

(21) Appl. No.: 14/804,601

(22) Filed: Jul. 21, 2015

(65) Prior Publication Data

US 2016/0015331 A1 Jan. 21, 2016

(30) Foreign Application Priority Data

Jul. 21, 2014 (DE) .................. 10 2014 214 104

(51) Int. Cl.
| | |
|---|---|
| *A61B 5/05* | (2006.01) |
| *A61B 5/00* | (2006.01) |
| *A61B 5/055* | (2006.01) |
| *A61B 5/107* | (2006.01) |
| *G01R 33/30* | (2006.01) |
| *G01R 33/54* | (2006.01) |

(52) U.S. Cl.
CPC ............ *A61B 5/7485* (2013.01); *A61B 5/055* (2013.01); *A61B 5/0555* (2013.01); *A61B 5/1072* (2013.01); *G01R 33/307* (2013.01); *G01R 33/543* (2013.01)

(58) Field of Classification Search
CPC .............................. A61B 5/00; A61B 5/7485
See application file for complete search history.

(56) References Cited

U.S. PATENT DOCUMENTS

| | | | |
|---|---|---|---|
| 2006/0034421 A1 | 2/2006 | Barkow et al. | |
| 2007/0053503 A1* | 3/2007 | Zelnik .................. | A61B 6/5235 378/205 |
| 2011/0297834 A1 | 12/2011 | Komori et al. | |
| 2015/0228071 A1 | 8/2015 | Jockel et al. | |

* cited by examiner

*Primary Examiner* — Tse Chen
*Assistant Examiner* — Jason Ip
(74) *Attorney, Agent, or Firm* — Schiff Hardin LLP

(57) ABSTRACT

In a method and imaging device for ascertaining an absolute scan region on a patient, who is positioned on an examination table, for a subsequent medical imaging examination by operation of the medical imaging device, the height of the patient is ascertained, a relative examination region is ascertained, and the absolute scan region of the patient for the subsequent medical imaging examination is determined in a processor using the patient height and the relative examination region.

3 Claims, 2 Drawing Sheets

METHOD FOR ASCERTAINING AN ABSOLUTE SCAN REGION ON A PATIENT

BACKGROUND OF THE INVENTION

Field of the Invention

The present invention relates to a method for ascertaining an absolute scan region on a patient, who is arranged on an examination table, for a subsequent medical imaging examination by operation of a medical imaging device.

Description of the Prior Art

In preparation for a medical imaging examination, in particular a magnetic resonance examination, by operation of a medical imaging device, in particular a magnetic resonance device, a reference position is conventionally detected by a light-beam localizer once a patient is positioned on an examination table of the medical imaging device. Using the reference position, an absolute scan region is then ascertained for the medical imaging examination by medical operating personnel. In conventional magnetic resonance examinations, this absolute scan region must be taken into account by the medical operating personnel as early as when ascertaining the reference position, and this frequently leads to errors in ascertaining the reference position and/or the absolute scan region. Furthermore, the conventional procedure is made more difficult due to the fact that the absolute scan region is also dependent on the height of the patient, and therefore this absolute scan region is designed differently for a magnetic resonance examination of the same region of the body on different patients.

SUMMARY OF THE INVENTION

An object of the present invention is to provide simple and error-free ascertainment of an absolute scan region for a medical imaging examination.

The invention is a method for ascertaining an absolute scan region on a patient, who is positioned on an examination table, for a subsequent medical imaging examination by a medical imaging device, that includes the steps of ascertaining a patient height, ascertaining a relative examination region, and determining the absolute scan region of the patient for the subsequent medical imaging examination of a processor, using the patient height and the relative examination region.

The relative examination region is preferably ascertained in relation to the patient height and is therefore independent of a reference point for the pending medical imaging examination. Particularly straightforward entry of examination variables that are easy to detect and/or are available for the medical operating personnel can be done by a medical operating personnel and an absolute scan region can be ascertained therefrom. Furthermore, a high level of operating convenience can be achieved in this way for medical operating personnel in preparation for the medical imaging examination. A predefined protocol can be used, moreover, without prior adjustment of the protocol to the height of the patient, so a work sequence for the medical operating personnel can be advantageously simplified.

The absolute scan region is preferably determined automatically by an arithmetic unit of the medical imaging device, with the patient height and the relative examination region forming part of the determination of the absolute scan region. The medical imaging device has evaluation software and/or evaluation computer programs that are required for this which are stored in a memory unit and can be run for a progression of the method for ascertaining an absolute scan region on a patient by a processor unit of the arithmetic unit. In addition, further variables that seem expedient to those skilled in the art can form part of the determination of the absolute scan region, such as a patient position on the examination table and/or an orientation of the patient on the examination table for the medical imaging examination. Alternatively or additionally, the absolute scan region can also be determined by loading and/or retrieving stored data records, which are stored for specific examinations of specific regions of the body, such as a medical imaging examination of a region of the lungs or a region of the heart.

The patient height is preferably ascertained manually by the medical operating personnel via a user interface of the medical imaging device, for example a keyboard together with a monitor, etc. Alternatively or additionally, the patient height can already be stored in a patient data record, so ascertaining the patient height can include loading and/or retrieving the stored patient data record. The relative examination region is likewise preferably ascertained manually by medical operating personnel via the user interface of the medical imaging device. Ascertaining the relative examination region can include a percentage value in relation to the height of the patient. For example, the relative examination region can include a region between 53% and 73% of the patient height. The relative examination region can also be ascertained by medical operating personnel using an examination region, for example a region of the liver or heart, and/or be automatically read by the arithmetic unit from a patient data record containing information on the pending imaging examination on the patient. A corresponding relative scan region can then be ascertained by the arithmetic unit of the medical imaging device since, in relation to the patient height, the relative examination region in the form of a percentage share and/or a percentage range is substantially the same.

The patient position is ascertained before the absolute scan region of the patient is calculated. The patient position is preferably ascertained and/or detected in relation to the examination table since, in particular, a position of the examination table during the medical imaging examination is known and a position of the patient relative to the examination table remains the same throughout the entire medical imaging examination preferably. Errors when preparing the absolute scan region for the medical imaging examination can be advantageously avoided, since the medical operating personnel can ascertain variables that are easy to detect for the calculation of the absolute scan region. The absolute scan region can be determined using the patient position.

The patient position can include an orientation of the patient on the examination table, for example whether the patient is positioned feet first or head first on the examination table for the pending magnetic resonance examination. The orientation of the patient can also be ascertained as a function of the type of examination and/or an examination region. By way of example, for an examination of the head of the patient using a medical imaging device, the patient is positioned head first on the examination table. The orientation of the patient can already be automatically ascertained in this way by the arithmetic unit by the medical operating personnel's choice of appropriate information for the pending medical imaging examination, so manual ascertainment by the medical operating personnel can advantageously be dispensed with, and therefore a further source of errors can be eliminated for the determination the absolute scan region of the patient.

The patient position can include spacing the patient from an edge region of the examination table. The absolute scan region can be ascertained particularly exactly in this way using the patient position together with the patient height and the relative examination region. The spacing of the patient from the edge region of the examination table is preferably specified in particular by markings. The examination table may therefore have pillows, for example, for positioning the patient, with these pillows including markings for positioning the head and/or for positioning the feet of the patient, with the pillows having an exactly defined position in relation to the patient positioning device.

In a further embodiment of the invention, the absolute scan region is calculated using a reference position. The reference position is preferably independent of a patient position, such as a standard reference point on the examination table. A fixed reference point for the medical imaging examination can be ascertained hereby independently of a patient position and/or a patient height. Furthermore, time-consuming detection and/or ascertaining of a reference point by means of a light-beam localizer, such as a laser sight, can advantageously be avoided, so a time-saving and simple patient preparation for the pending medical imaging examination can be achieved. The reference position can be, for example, an edge region and/or an edge region of the examination table and/or further reference positions that seem expedient to those skilled in the art.

In a further development of the invention, ascertaining the relative examination region includes entering a start value of the relative examination region and/or entering an end value of the relative examination region into the processor. Medical operating personnel can employ a simple estimate using the height of the patient for the relative examination region and make the results of this estimate directly available to the system via the user interface for determination of the absolute scan region. Errors that occur in the case of a complex conversion of the relative examination region into an absolute scan region by the medical operating personnel can be avoided in this way. Furthermore, particularly time-saving entry of parameters by the medical operating personnel for determining the absolute scan region may also be achieved in this way. The start value can include a spacing of a start position of the relative examination region from a reference value and/or a start position in relation to the patient height. The end value can likewise include a spacing of an end position from a reference value and/or an end position in relation to the patient height.

Alternatively or additionally, a length of the relative examination region of the patient can be detected. The length of the relative examination region can be detected manually by the medical operating personnel by the operator communicating the length of the relative examination region with a start and/or an end value via the user interface to the medical imaging device, in particular the arithmetic unit. Using the length of the relative examination region a length of the absolute scan region can be ascertained, it being possible for the length of the relative examination region to be equal to the length of the absolute scan region. The length of the absolute scan region of the patient is preferably ascertained automatically by the arithmetic unit of the medical imaging device. Furthermore, the absolute scan region can already be ascertained by the arithmetic unit from the length and a start value or an end value.

In a further embodiment of the invention, ascertaining the relative examination region includes retrieving predefined and/or stored values for the relative examination region. The relative examination region can be ascertained particularly quickly and easily in this way and errors during ascertainment by the medical operating personnel can therewith advantageously be avoided. Predefined and/or stored values can be provided in this connection for the relative examination region in particular for examinations on the patient which include a defined organ or a number of defined organs and/or a defined region of the patient. The defined organ and/or the defined region of the patient can include, for example, a region of the liver and/or heart and/or the whole body, etc. of the patient. For example, a region of the liver in different patients is always situated between 53% and 73% in relation to the height of the patient. This region specification is independent of the height of the patient and thus is applicable to all patients for whom an examination of the liver with the medical imaging device is pending. The absolute scan region can be automatically ascertained by the arithmetic unit by means of the stored data due to such entry of an examination region for the patient by the medical operating personnel.

The invention also encompasses a medical imaging device, having a system control computer, a detector unit and a patient positioning device having an examination table. The medical imaging device is designed to carry out a method for ascertaining an absolute scan region on a patient, who is positioned on the examination table, for a subsequent medical imaging examination, having the steps of ascertaining a patient height, ascertaining a relative examination region, and a processor configured to determine the absolute scan region of the patient for the subsequent medical imaging examination using the patient height and the relative examination region.

Particularly easy entry of examination variables by medical operating personnel can occur and an absolute scan region can be ascertained therefrom. The relative examination region is preferably ascertained in relation to the patient height and is therefore independent of a reference point for the pending medical imaging examination. Furthermore, a high level of operating convenience can be achieved in this for way medical operating personnel in preparation for the medical imaging examination. A predefined protocol can be used, moreover, without prior adjustment of the protocol to the height of the patient, whereby a work sequence for the medical operating personnel can be advantageously simplified.

The system control computer includes an arithmetic unit which, together with appropriate software and/or appropriate computer programs, is designed to carry out the inventive method for ascertaining an absolute scan region on a patient. The arithmetic unit is a processor with which computer programs and/or software is/are run. In addition, the arithmetic unit can have a memory unit in which the computer programs and/or the software is/are stored.

The advantages of the inventive medical imaging device substantially correspond to the advantages of the inventive method for ascertaining an absolute scan region on a patient that have been stated above in detail.

The present invention also encompasses a non-transitory, computer-readable data storage medium encoded with programming instructions that, when the storage medium is loaded into a control computer of a medical imaging apparatus, cause the control computer to implement any or all of the above-described embodiments of the method according to the invention.

DESCRIPTION OF THE PREFERRED EMBODIMENTS

Figure 1:
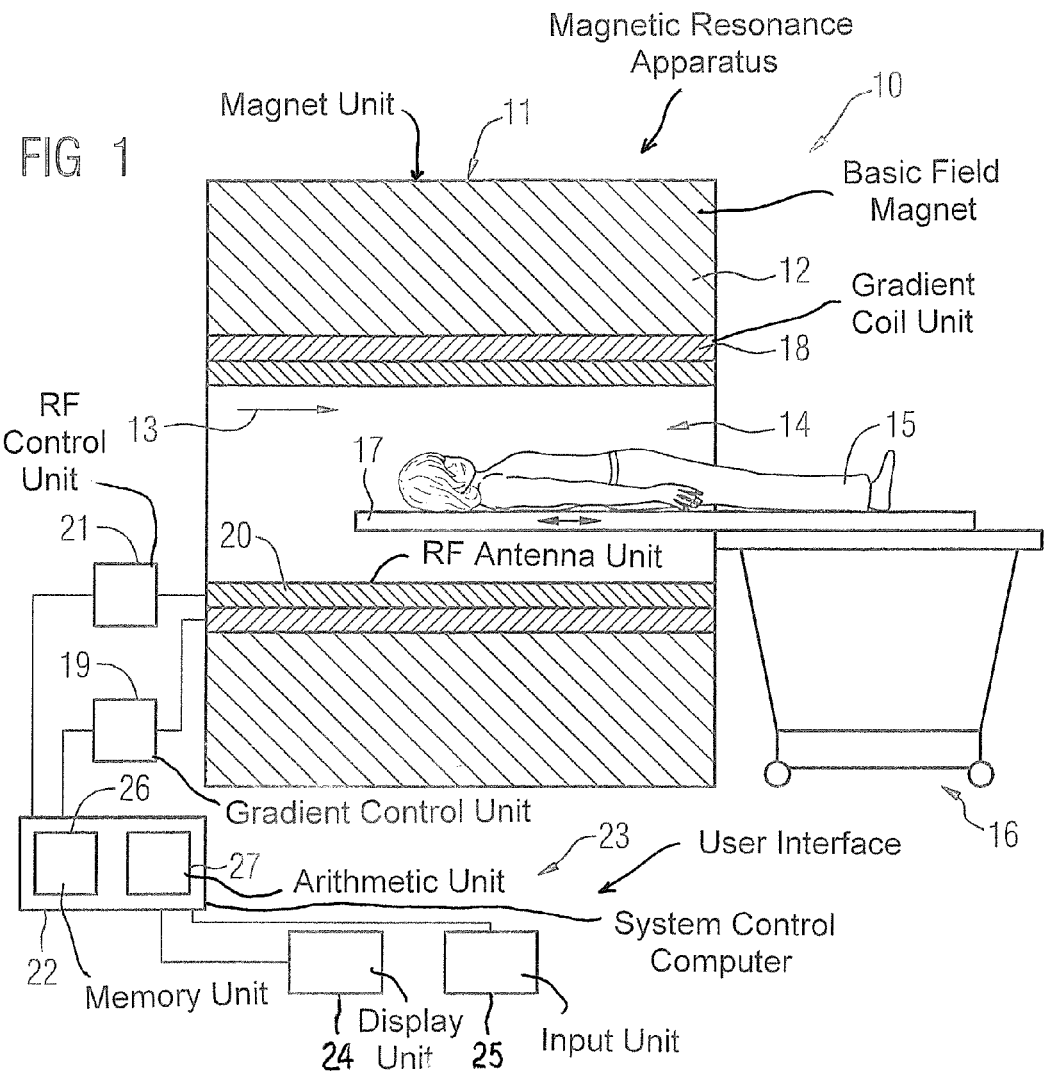
FIG. 1 schematically illustrates an inventive medical imaging apparatus in a schematic view.

FIG. 1 schematically shows a medical imaging device. In the present exemplary embodiment the medical imaging device is formed by a magnetic resonance apparatus 10. The embodiment of the medical imaging device is not limited to a magnetic resonance apparatus 10, however. Instead the medical imaging apparatus can be formed by any medical imaging apparatus that seems expedient to those skilled in the art, such as by a computed tomography apparatus, a positron-emission tomography apparatus, etc.

The magnetic resonance apparatus 10 has a magnet unit 11 that includes a super-conducting basic field magnet 12 for generating a strong and constant main basic magnetic field 13. Furthermore, the magnetic resonance apparatus 10 has a patient-receiving region 14 for receiving a patient 15. The patient-receiving region 14 in the present exemplary embodiment is cylindrical and cylindrically surrounded in a circumferential direction by the magnet unit 11. Basically, however, a design of the patient-receiving region 14 that is different is conceivable. The patient 15 can be moved by a patient positioning device 16 of the magnetic resonance apparatus 10 into the patient-receiving region 14. The patient positioning device 16 has for this purpose an examination table 17 designed to be moved inside the patient-receiving region 14.

The magnet unit 11 also has a gradient coil unit 18 for generating magnetic field gradients which are used for spatial encoding during imaging. The gradient coil unit 18 is controlled by means of a gradient control computer 19 of the magnetic resonance apparatus 10. The magnet unit 11 also has a radio-frequency antenna unit 20 for exciting a polarization that is established in the main magnetic field 13 generated by the basic field magnet 12. The radio-frequency antenna unit 20 is controlled by a radio-frequency (RF) antenna control unit 21 of the magnetic resonance apparatus 10 and emits radio-frequency magnetic resonance sequences into an examination space, which is substantially formed by a patient-receiving region 14 of the magnetic resonance apparatus 10.

To control the basic field magnet 12, the gradient control unit 19 and to control the radio-frequency antenna control unit 21, the magnetic resonance apparatus 10 has a system control computer 22. The system control computer 22 centrally controls the magnetic resonance apparatus 10, such as for the performance of a pre-determined imaging gradient echo sequence. Furthermore, the system control unit 22 has an evaluation unit (not shown) for evaluating medical image data that are acquired during the magnetic resonance examination. The magnetic resonance apparatus 10 also has a user interface 23 that is connected to the system control computer 22. Control information such as imaging parameters and reconstructed magnetic resonance images can be displayed for medical operating personnel on a display unit 24, for example on at least one monitor, of the user interface 23. The user interface 23 also has an input unit 25, via which information and/or parameters can be entered by the medical operating personnel during a measuring process.

Before a magnetic resonance examination can be carried out on the patient 15, the patient 15 must firstly be positioned on the examination table 17. In addition, an absolute scan region R_Abs of the patient 15 must be ascertained for the pending magnetic resonance examination. This absolute scan region R_Abs ascertains a region of the patient 15 from which medical image data are to be acquired by magnetic resonance scans of the pending magnetic resonance examination.

Figure 2:
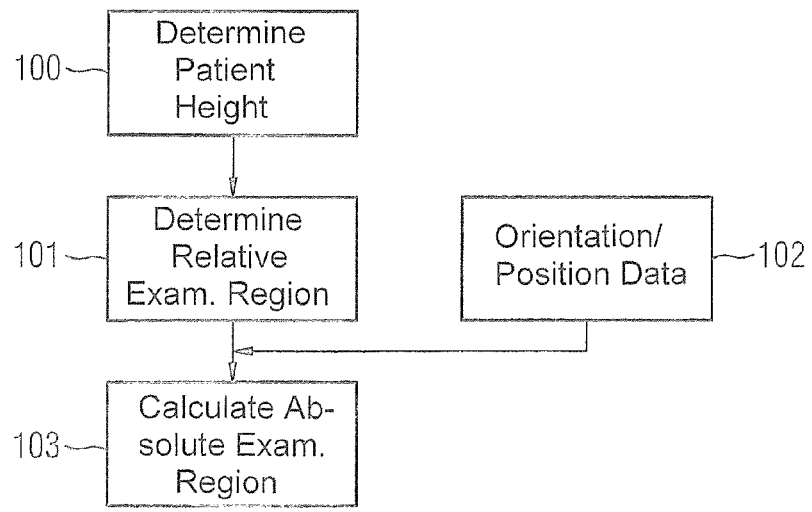
FIG. 2 is a flowchart of the inventive method for ascertaining an absolute scan region on a patient.

FIG. 2 shows a flowchart of an inventive method for ascertaining an absolute scan region R_Abs on a patient 15, who is positioned on the examination table 17, for a subsequent medical imaging examination, in the present exemplary embodiment for a magnetic resonance examination. The method is performed by the system control computer 22 of the magnetic resonance apparatus 10, with the system control computer 22 having a memory unit 26 and an arithmetic unit 27 with a processor unit (not shown) for this purpose. Furthermore, the system control computer 22 has evaluation software and/or evaluation computer programs that are required for this and are stored in the memory unit 26 and are executed for a progression of the method for ascertaining an absolute scan region on the patient 15 by the processor unit of the arithmetic unit 27.

For this purpose, a height H of the patient is firstly ascertained in a first method step 100. The patient height H can be provided manually by medical operating personnel via the input unit 25 of the magnetic resonance apparatus 10, in particular the system control computer 22. Furthermore, ascertainment of the patient height H may also include calling up and/or loading of a stored patient data record, in which the patient height H is stored. The patient height H preferably includes the body size of the patient 15.

In a further method step 101 a relative examination region R_Rel of the patient 15 is ascertained. The relative examination region R_Rel can likewise be ascertained manually by the medical operating personnel via the input unit 25. The relative examination region R_Rel can be ascertained by the medical operating personnel in relation to the patient height H, in particular input, such as in the form of a percentage value of the relative examination region R_Rel in relation to the height H of the patient 15. For example, the relative examination region R_Rel for an examination of the liver on the patient 15 can be a region between 53% and 73% of the patient height H.

Figure 5:
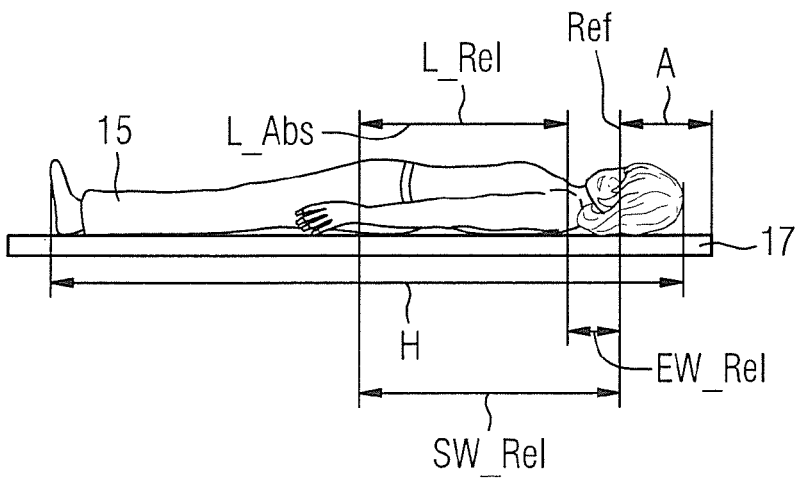
FIG. 5 is a schematic view of a relative examination region on a patient.

The relative examination region R_Rel can also be ascertained by the medical operating personnel by means of an input of a relative start value SW_Rel of the relative examination region R_Rel and/or by means of an input of a relative end value EW_Rel of the relative examination region R_Rel. The relative start value SW_Rel and/or the relative end value EW_Rel of the relative examination region R_Rel are preferably in relation to the height H of the patient 15. Alternatively or additionally, the relative start value SW_Rel and/or the relative end value EW_Rel of the relative examination region R_Rel can also be ascertained in relation to a reference point, such as in relation to an edge and/or an edge region of the examination table 17 etc., as is also shown in FIG. 5.

Using the relative start value SW_Rel and the relative end value EW_Rel a length L_Rel of the relative examination region R_Rel can be determined which matches a length L_Abs of the absolute scan region R_Abs. In addition, the length L_Rel of the relative examination region R_Rel together with the relative start value SW_Rel or the relative end value EW_Rel can be ascertained by the medical operating personnel.

Figure 3:
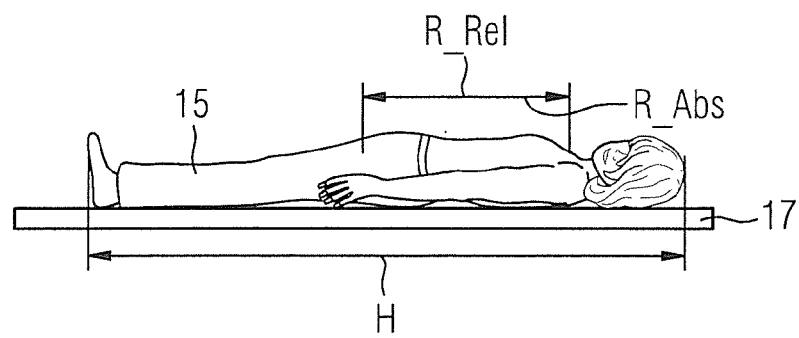
FIG. 3 illustrates a determination of an absolute scan region on a first patient in a schematic view.
Figure 4:
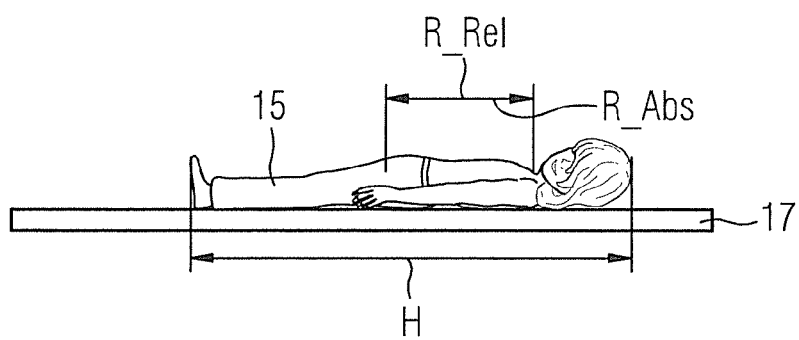
FIG. 4 illustrates a determination of an absolute scan region on a second patient in a schematic view.

It is also conceivable, moreover, for medical operating personnel to only ascertain a section that is to be examined of the patient 15 in this method step 101, in particular to ascertain this section on an organ, such as on a region of the liver and/or heart, of the patient 15. This section can include a defined examination region and/or a defined organ of the patient 15. The choice of relative examination region R_Rel can then be made automatically by means of the arithmetic unit 27 of the system control computer 22 using the ascertained section that is to be examined. This defined examination region of the patient 15 can be ascertained by the medical operating personnel as a percentage value of this region, in particular in relation to the height H of the patient. These percentages can be read by way of example from a table, since, in relation to the patient height H, the relative examination region R_Rel in the form of a percentage share and/or a percentage range remains the same in each case, as can be seen in FIGS. 3 and 4. FIGS. 3 and 4 show the relative examination region R_Rel for two patients 15 of different heights. Due to the different heights H of the patients 15 in FIGS. 3 and 4 a percentage value of the relative examination region R_Rel in relation to the patient height H remains the same but the absolute scan region R_Abs of the respective patient 15 that results therefrom varies.

Furthermore it is also conceivable for just the disclosure and/or ascertainment of a defined examination region and/or body region of the patient 15 to be made by medical operating personnel, and the arithmetic unit 27 automatically ascertains start values and/or end values of the relative examination region R_Rel using this disclosure. For this purpose, the arithmetic unit 27 preferably uses examination data and/or allocations of organ regions to a human body stored and/or saved inside the memory unit 26.

If the relative examination region R_Rel is automatically ascertained by the arithmetic unit 27 by retrieving predefined values and/or stored data, it may also be provided that this stored data also already includes a predefined position of the patient 15. This data can be, for example, an orientation and/or position of the patient 15 relative to the examination table 17. For examinations of the head by way of example, the patient 15 is positioned on the examination table 17 head first. Furthermore, even when using a local head coil a position of the patient 15 is ascertained on the basis of a predefined position of the local head coil on the examination table 17.

If this information does not yet exist, it must be ascertained by medical operating personnel in a further method step 102 before the absolute scan region R_Abs of the patient 15 is calculated by means of the user interface 23. For this purpose the medical operating personnel must ascertain an orientation of the patient 15 in relation to the examination table 17, whether he/she is positioned feet and/or head first on the examination table 17. Furthermore, a spacing A of the patient 15 from an edge region of the examination table 17 is also ascertained in this method step 102, with the spacing A having already been predetermined. The spacing A of the patient 15 from the edge region of the examination table 17 is predefined by markings in particular. The examination table 17 can therefore include cushions, for example, for positioning the patient 15, with these cushions having markings for positioning a head and/or for positioning the feet of the patient 15. These markings have an exactly defined position in relation to the patient positioning device 16, in particular the examination table 17.

Using the acquired patient height H and the relative examination region R_Rel the absolute scan region R_Abs is calculated by the arithmetic unit 27 in a further method step 103. A length L_Abs of the absolute scan region R_Abs and an absolute start value SW_Abs of the absolute scan region R_Abs is determined by the arithmetic unit 27.

The absolute start value SW_Abs is calculated as follows by the arithmetic unit 27:

$$SW_{Abs} = -1\left(H - H\frac{EW\_Rel}{100} - (Ref - A)\right).$$

The absolute length L_Abs of the absolute scan region R_Abs is determined as follows:

$$L_{Abs} = -H\frac{EW\_Rel - SW\_Rel}{100}.$$

Here Ref is the reference position, in relation to which the absolute scan region (R_Abs), in particular the absolute start value SW_Abs and the absolute length L_Abs of the absolute scan region R_Abs, is determined. In the present exemplary embodiment (FIG. 5) the reference position is ascertained at the center of the head of the patient 15. Basically any other ascertainment of the reference position that seems expedient to those skilled in the art is always possible, however.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance (MR) data from a patient, comprising:

providing an examination table of an MR data acquisition scanner with a marking on the examination table at a spacing A from an edge of the examination table, said examination table being movable in a longitudinal direction of said MR scanner;

placing a patient on the examination table at a patient position Ref relative to said marker on said examination table;

providing a control computer with an electronic input that designates a height H of the patient and with another electronic input that designates a section of the patient, said section of the patient being selected from the group consisting of a defined examination region of the patient and a defined organ of the patient;

in said control computer, accessing a database, after placing the patient at said patient position on said examination table, that correlates said section with said patient of said height H and, dependent on said correlation, calculating, as a range or percentage of said height H of said patient, a relative examination region that encompasses said section within said patient, said relative examination region having a start SW_Rel and an end EW_Rel in said longitudinal direction and a relative examination region length between said start and said end that is said range or percentage of said height H of said patient;

in said control computer, determining a final examination region in said scanner, from which MR image data will be acquired, said final examination region having a final examination region start $SW_{Abs}$ at which acquisition of said medical image data by said scanner begins, and a final examination region end $EW_{Abs}$ at which said acquisition of said medical image data by said scanner ceases, said final examination region and being at a length $L_{Abs}$ from said final examination region start $SW_{Abs}$, according to:

$$SW_{Abs} = -1\left(H - H\frac{EW_{Rel}}{100} - (Ref - A)\right), \text{ and}$$

$$L_{Abs} = -H\frac{EW\_Rel - SW\_Rel}{100};$$

and
with said control computer, operating said MR scanner to acquire said MR image data from said final examination region, and making the acquired MR data available in electronic form as an output from said control computer.

2. A magnetic resonance (MR) imaging apparatus comprising:
an MR data acquisition;
an examination table movable in a longitudinal direction into and out of said MR scanner, said examination table having a marker therein at a spacing A from an edge of the examination table, and being adapted to receive a patient thereon at a patient position Ref relative to said marker on said examination table;
a control computer configured to operate said scanner in order to acquire MR image data from said patient;
said control computer being configured to receive an electronic input that designates a height H of the patient and another electronic input that designates a section of the patient, said section of the patient being selected from the group consisting of a defined examination region of the patient and a defined organ of the patient;
after placing the patient at said patient position on said examination table, said control computer being configured to access a database that correlates said section with said height of said patient and, dependent on said correlation, to calculate, as a range or percentage of said height of said patient, a relative examination region that encompasses said section within said patient, said relative examination region having a start SW_Rel and an end EW_Rel in said longitudinal direction and a relative examination region length between said start and said end that is said range or percentage of said height H of said patient;
said control computer being configured to determine a final examination region in said scanner, from which said MR image data will be acquired, along said longitudinal direction, said final examination region having a final examination region start $SW_{Abs}$ at which acquisition of said medical image data by said scanner begins, and a final examination region end $EW_{Abs}$ at which said acquisition of said medical image data by said scanner ceases said final examination region and being at a length $L_{Abs}$ from said final examination region start $SW_{Abs}$, according to:

$$SW_{Abs} = -1\left(H - H\frac{EW_{Rel}}{100} - (Ref - A)\right), \text{ and}$$

$$L_{Abs} = -H\frac{EW\_Rel - SW\_Rel}{100};$$

and
said control computer being configured to operate said MR scanner to acquire said MR image data from said final examination region, and to make the acquired MR data available in electronic form as an output from said control computer.

3. A non-transitory, computer-readable data storage medium encoded with programming instructions, said storage medium being loaded into a control computer of a magnetic resonance MR apparatus that comprises an MR data acquisition scanner and an examination table movable in a longitudinal direction into and out of said MR scanner, said examination table having a marker therein at a spacing A from an edge of the examination table, and being adapted to receive a patient thereon at a patient position Ref relative to said marker on said examination table, said programming instructions causing said control computer to:
receive an electronic input that designates a height H of the patient and another electronic input that designates a section of the patient, said section of the patient being selected from the group consisting of a defined examination region of the patient and a defined organ of the patient;
after placing the patient at said patient position on said examination table, access a database that correlates said section with said height of the patient and, dependent on said correlation, calculating, as a range or percentage of said height of said patient, a relative examination region that encompasses said section within said patient, said relative examination region having a start SW_Rel and an end EW_Rel in said longitudinal direction and a relative examination region length between said start and said end that is said range or percentage of said height H of said patient;
determine a final examination region in said scanner, from which said MR image data will be acquired along said longitudinal direction, said final examination region having a final examination region start $SW_{Abs}$ at which acquisition of said medical image data by said scanner begins, and a final examination region end $EW_{Abs}$ at which said acquisition of said medical image data by said scanner ceases, said final examination region and being at a length $L_{Abs}$ from said final examination region start $SW_{Abs}$, according to:

$$SW_{Abs} = -1\left(H - H\frac{EW_{Rel}}{100} - (Ref - A)\right), \text{ and}$$

$$L_{Abs} = -H\frac{EW\_Rel - SW\_Rel}{100};$$

and
operate said MR scanner to acquire said MR image data from said final examination region, and make the acquired MR data available in electronic form as an output from said control computer.

* * * * *